United States Patent
Shamilov et al.

(10) Patent No.: US 11,482,338 B2
(45) Date of Patent: Oct. 25, 2022

(54) SIMULATION OF HEART PACING FOR MODELING ARRHYTHMIA

(71) Applicant: BIOSENSE WEBSTER (ISRAEL) LTD., Yokneam (IL)

(72) Inventors: Elias Shamilov, Eshhar (IL); Vladimir Rubinstein, Haifa (IL); Shiran Eliyahu, Yokneam Illit (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 134 days.

(21) Appl. No.: 15/913,483

(22) Filed: Mar. 6, 2018

(65) Prior Publication Data

US 2019/0279773 A1    Sep. 12, 2019

(51) Int. Cl.
| | |
|---|---|
| *A61B 5/00* | (2006.01) |
| *G16H 50/50* | (2018.01) |
| *A61B 5/0538* | (2021.01) |
| *G16H 20/30* | (2018.01) |
| *G16H 40/63* | (2018.01) |
| *A61B 5/319* | (2021.01) |
| *A61B 5/349* | (2021.01) |

(52) U.S. Cl.
CPC .......... *G16H 50/50* (2018.01); *A61B 5/0538* (2013.01); *A61B 5/319* (2021.01); *A61B 5/349* (2021.01); *G16H 20/30* (2018.01); *G16H 40/63* (2018.01)

(58) Field of Classification Search
CPC .............. A61B 5/04012; A61B 5/0402; A61B 5/04021; A61B 5/04028; A61B 5/0432; A61B 5/04325; A61B 5/044; A61B 5/0452; A61B 5/04525; A61B 5/046; A61B 5/7264; A61B 5/7267; A61B 5/7278; A61B 5/742; A61B 5/743
See application file for complete search history.

(56) References Cited

U.S. PATENT DOCUMENTS

| | | | |
|---|---|---|---|
| 5,041,973 A | | 8/1991 | Lebron et al. |
| 5,722,416 A | * | 3/1998 | Swanson .............. A61B 5/0422 600/509 |
| 7,828,735 B2 | | 11/2010 | Holmes et al. |
| 8,805,504 B2 | | 8/2014 | Sweeney |
| 9,050,011 B2 | | 6/2015 | Rubinstein et al. |
| 2005/0202384 A1 | | 9/2005 | DiCuccio et al. |
| 2014/0022250 A1* | | 1/2014 | Mansi .................... G06T 19/20 345/420 |

(Continued)

OTHER PUBLICATIONS

European Search Report dated Jul. 8, 2019 for corresponding EPA No. 19160745.6.

*Primary Examiner* — Eugene T Wu
(74) *Attorney, Agent, or Firm* — Dergosits & Noah LLP; Todd A. Noah

(57) ABSTRACT

A cardiac simulation method includes storing, in a memory, a measured electrophysiological (EP) map of at least part of wall tissue of a heart of a patient. Based on the stored EP map, simulated electrical activity in response to computer-simulated pacing, which simulates actual electrical activity that would occur across the wall tissue of the heart of the patient in response to actual pacing, is calculated in a processor. Based on the simulated electrical activity calculated in the processor, one or more candidate locations on the wall tissue of the heart at which arrhythmia is suspected of originating are identified and indicated to a user.

14 Claims, 2 Drawing Sheets

(56) References Cited

U.S. PATENT DOCUMENTS

| | | |
|---|---|---|
| 2015/0242589 A1 | 8/2015 | Neumann et al. |
| 2015/0294082 A1 | 10/2015 | Passerini |
| 2015/0371437 A1 | 12/2015 | Mansi et al. |
| 2016/0022375 A1 | 1/2016 | Blake |
| 2016/0058520 A1* | 3/2016 | Yang .................. G16H 50/50 703/11 |
| 2017/0185740 A1 | 6/2017 | Seegerer |
| 2017/0281031 A1 | 10/2017 | Houben et al. |

* cited by examiner

SIMULATION OF HEART PACING FOR MODELING ARRHYTHMIA

FIELD OF THE INVENTION

The present invention relates generally to medical simulations, and particularly to simulations of an electrophysiological activity of a heart.

BACKGROUND OF THE INVENTION

Cardiac procedures often employ techniques to isolate potential sources of cardiac arrhythmia in a heart tissue. For example, U.S. Pat. No. 5,722,416 describes systems and methods for analyzing biopotential morphologies in body tissue. The systems and methods use a template of a biopotential event of known cause in body tissue. The template comprises a plot of variations in biopotentials over time. The systems and methods compare this template to a sample of a biopotential event externally triggered in body tissue. The sample comprises a plot of variations in biopotentials over time. The systems and methods generate an output based upon the comparison. The systems and methods can be used to compare an event-specific template of a cardiac event of known diagnosis to a sample of a paced cardiac event. The comparison yields a matching factor indicating how alike the input sample is to the input template. The systems and methods compare the matching factor to a predetermined value to determine the location of sites that are potentially appropriate for ablation. A matching factor that indicates close similarity between the sample and the template suggests that the pacing site lies close to a region potentially appropriate for ablation to treat the arrhythmia.

As another example, U.S. Pat. No. 5,041,973 describes a cardiac mapping system simulator comprising a microprocessor for simulating the electrical signal propagation of a heartbeat as it moves across the surface of a heart. A series of impulses that mimic the electrophysiological waveform are generated forming a two-dimensional map depicting heart activity. The series of pulses are generated in accordance with predetermined patterns and applied to the inputs of a cardiac mapping system or electrophysiology lab equipment in order to assess the operating condition of the cardiac mapping system or electrophysiology lab equipment prior to use on patients.

U.S. Patent Application Publication 2015/0371437 describes a system and method for visualization of cardiac changes under various pacing conditions for intervention planning and guidance is disclosed. A patient-specific anatomical heart model is generated based on medical image data of a patient. A patient-specific computational model of heart function is generated based on patient-specific anatomical heart model. A virtual intervention is performed at each of a plurality of positions on the patient-specific anatomical heart model using the patient-specific computational model of heart function to calculate one or more cardiac parameters resulting from the virtual intervention performed at each of the plurality of positions. One or more outcome maps are generated visualizing, at each of the plurality of positions on the patient-specific anatomical heart model, optimal values for the one or more cardiac parameters resulting from the virtual intervention performed at the that position on the patient-specific anatomical heart model.

SUMMARY OF THE INVENTION

An embodiment of the present invention provides a medical method including storing, in a memory, a measured electrophysiological (EP) map of at least part of wall tissue of a heart of a patient. Based on the stored EP map, simulated electrical activity in response to computer-simulated pacing, which simulates actual electrical activity that would occur across the wall tissue of the heart of the patient in response to actual pacing, is calculated in a processor. Based on the simulated electrical activity calculated in the processor, one or more candidate locations on the wall tissue of the heart at which arrhythmia is suspected of originating are identified and indicated to a user.

In some embodiments, the method includes storing one or more of a Local Activation Time (LAT) map, a voltage map and an adjusted LAT map, and wherein the one or more locations include electro-anatomical locations on the EP maps.

In some embodiments, the method includes identifying the one or more candidate locations by comparing the simulated electrical activity with the actual electrical activity, which was acquired in the heart of the patient and which exhibits the arrhythmia, and finding the candidate locations that produce a best fit between the simulated electrical activity and the actual electrical activity.

In an embodiment, the method includes finding a best temporal fit between the simulated electrical activity and the actual electrical activity.

In another embodiment, the method further includes assigning the one or more candidate locations respective grades that quantify a likelihood of the candidate locations being sources of the arrhythmia.

In some embodiments, the method further includes presenting the grades assigned to the one or more candidate locations to a user.

In some embodiments, the method includes updating the EP map with the grades assigned to the one or more candidate locations.

In an embodiment, the method includes receiving, via a user interface, user input indicative of the one or more candidate locations.

There is additionally provided, in accordance with an embodiment of the present invention, a cardiac pacing simulator, including a memory and a processor. The memory is configured to store a measured electrophysiological (EP) map of at least part of wall tissue of a heart of a patient. The processor is configured to calculate, based on the stored EP map, simulated electrical activity in response to computer-simulated pacing, which simulates actual electrical activity that would occur across the wall tissue of the heart of the patient in response to actual pacing. The processor is further configured to, based on the simulated electrical activity calculated in the processor, identify and indicate to a user one or more candidate locations on the wall tissue of the heart, at which arrhythmia is suspected of originating.

The present invention will be more fully understood from the following detailed description of the embodiments thereof, taken together with the drawings in which:

DETAILED DESCRIPTION OF EMBODIMENTS

Overview

Figure 1:
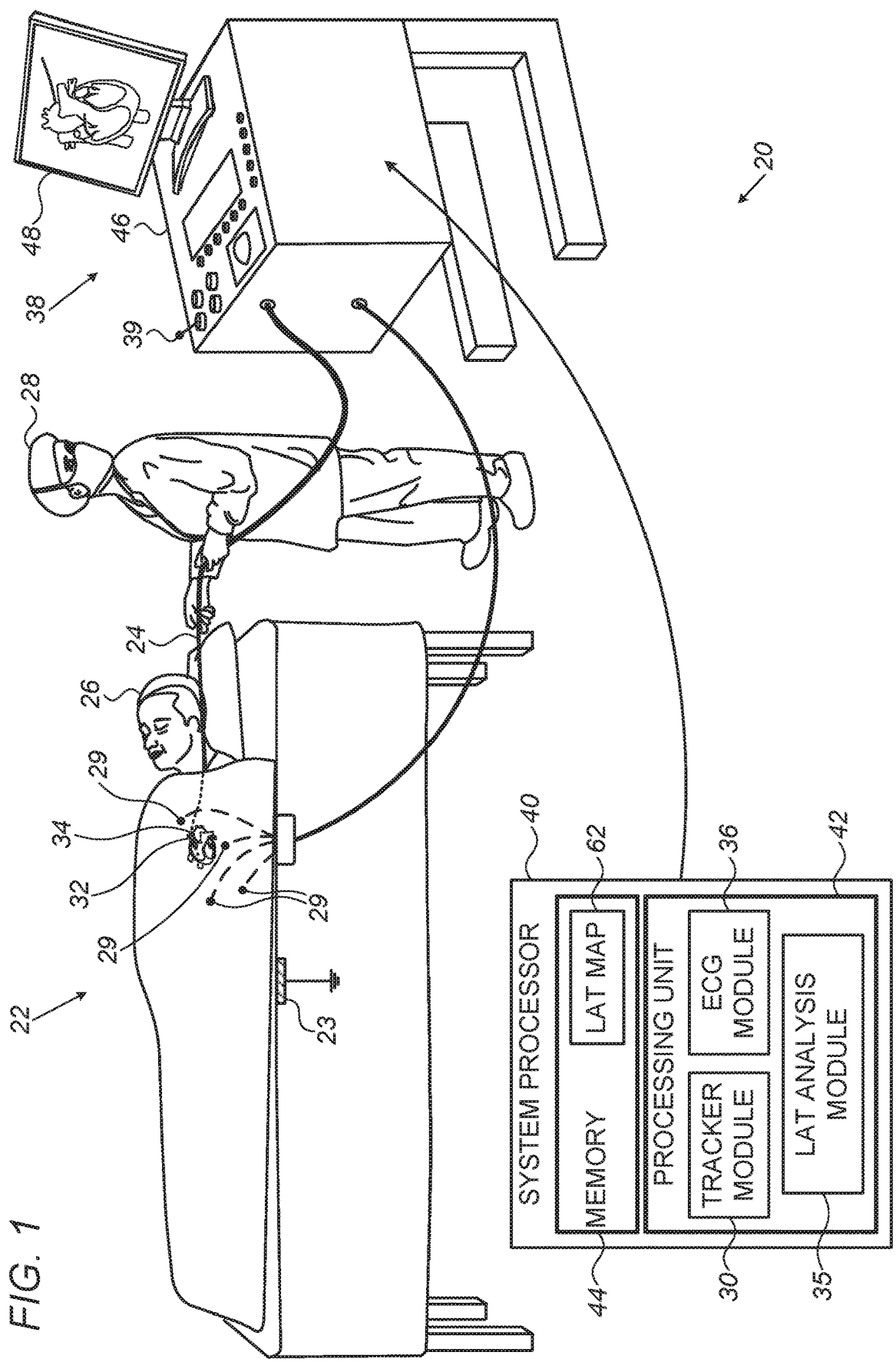
FIG. 1 is a schematic, pictorial illustration of a cardiac 3D navigation and electrophysiological signal analysis system, in accordance with an embodiment of the present invention.

Embodiments of the present invention that are described herein provide a cardiac simulator and a simulation method for identifying, estimating and grading locations on the cardiac surface from which an arrhythmia may originate.

Cardiac arrhythmia, which is defined as a variation from the normal heart rate and/or rhythm, may belong to several categories. One category is characterized by an enhanced or abnormal impulse formation (from locations at heart tissue of abnormal focal activity). Another category is characterized by disturbances in electrical conduction at various possible locations over the heart surface.

One possible way to find the location from which an arrhythmia originates is to stimulate selected locations on the cardiac surface of a patient with electrical signals, in an attempt to generate actual arrhythmia that matches pre-recorded arrhythmia of that patient. The quality of match may consider factors such as morphology, sequence and relevant time intervals that are measured on the system. The underlying assumption is that treating such a location, e.g., by applying ablation, is likely to reduce or eliminate the arrhythmia in question. The invasive diagnostic procedure described above is called "pacing," while the process of the comparison is called "pace mapping." Pacing is typically a lengthy process, as it typically has to be repeated manually over numerous locations in the heart.

In some embodiments of the present invention, the above-described pacing procedure is replaced by computerized simulation, also referred to herein as "virtual pacing." In some embodiments, a cardiac simulator comprises a processor that stores a pre-acquired electrophysiological map of at least a portion of heart surface of a patient. One example of such an electrophysiological map is referred to herein as a Local Activation Time (LAT) map. A LAT map characterizes the time-dependent propagation of an initiated electrical signal (potential), which flows through the cardiac muscle and connective tissue comprising the heart, as further explained below.

A variant of the LAT map is also in use in some embodiments of the present invention, and is named herein after 'adjusted LAT map.' Adjusted LAT maps are LAT maps optimized to increase coherence, as described in U.S. Pat. No. 9,050,011 and in U.S. Patent Application Publication 2017/0281031, which are assigned to the assignee of the present patent application and whose disclosures are all incorporated herein by reference. Another example of such an electrophysiological map is referred to herein as a voltage map, in which the electrical voltage of each electro-anatomical location is registered and translated into a color-coded map to identify areas of sick tissue, healthy tissue and scar. In an embodiment, the calculation of simulated pacing is performed using a LAT map only, without using any other type of maps. In some embodiment the source placement of the candidates for virtual pacing can be defined using also voltage map. For example, the good candidates are border zone of a scar or isthmus area.

In another embodiment of the current invention, one or more than one LAT map can be used. For example, one LAT map that is built during sinus rhythm and another LAT map that was built during some arrhythmia or during pacing.

In order to identify locations from which an arrhythmia may originate, the processor simulates the propagation of electrical activity, from one or more candidate locations on the LAT map using additional inputs from the voltage map and the adjusted LAT map. The processor simulates such activity in a process named hereinafter 'simulated pacing.' The processor calculates, at various locations on the LAT and/or adjusted LAT map, propagation of the electrical activity resulting from the one or more virtually paced potentials.

The processor typically builds a new LAT map based on the selected position of the initial virtual pace and the approximated time differences between this position and each point of the anatomical mesh considering electric wave propagation:

Start time (t=0) is defined as the activation time at the selected position of the simulated pacing.

Calculation of the arrival time of the propagated electrical wave to all points at the anatomical mesh, based on real LAT map or maps differences and/or calculated based on the improvements added to the LAT map using the adjusted LAT map application.

The processor then compares the simulated electrical activity resulting from simulation with the actual time intervals of the clinical recorded arrhythmia (i.e., fading time of the electrical conductivity through the cardiac chamber).

In an embodiment, the processor further assigns grades to virtually paced locations that quantify a likelihood of the candidate locations being sources of the arrhythmia based on the comparison of measured time intervals. The physician may utilize the grades to optimize subsequent diagnostics and therapeutics steps.

Performing simulated pacing according to the disclosed technique directs the physician to the probable locations that an arrhythmia may initiate from. Therefore, the simulation may reduce the number of pacing steps that the physician needs to perform during an invasive procedure. Furthermore, the disclosed technique is free of time limitations and other constraints associated with the actual invasive pacing procedure (such as moving the catheter between pacing locations which might require maneuvering of the catheter to difficult-to-reach locations or areas of the heart where it is also difficult to stabilize the catheter). Thus, the disclosed systems and methods may increase the probability of the physician succeeding in a subsequent invasive cardiac treatment. Moreover, the simulation may rule out numerous locations in heart tissue from being considered candidate origins of an arrhythmia, and direct the physician to other causes of the arrhythmia, possibly shortening procedure time and simplifying workflow.

The disclosed technique of simulated pacing has the potential advantage of shortening the duration of an invasive diagnostic procedure, and decreasing hand fatigue and difficult maneuvering of the catheter by incorporating into the procedure steps of "virtual pacing" on the computer screen instead of by moving the catheter to a desired location and pacing by the catheter. Additionally, the disclosed technique has the potential of reducing the pace burden on the patient's heart and avoiding a potential risk of long term cardiac remodeling, as well as the risk of triggering a patient's hemodynamically unstable arrhythmia which might risk the patient's life.

System Description

FIG. 1 is a schematic, pictorial illustration of a cardiac 3D navigation and electrophysiological signal analysis system 20, in accordance with an embodiment of the present invention. System 20 may be configured to analyze substantially any physiological parameter or combinations of such parameters. In the description herein, by way of example, the signals analyzed are assumed to be intra-cardiac (IC) and/or extra-cardiac (body surface—BS) electrocardiogram (ECG) potential-time relationships. In order to fully characterize such relationships, the signals at various locations need to be referenced in time to each other, such as is done during generating a LAT map. The time referencing is accomplished by measuring relative to a reference-time (e.g., instance), such as the beginning of each QRS complex of an ECG reference signal (i.e., the beginning of every heartbeat). The method for generating a LAT map is described in U.S. Pat. No. 9,050,011, cited above.

For simplicity and clarity, the following description, except where otherwise stated, assumes an investigative procedure wherein system 20 measures actual electrical activity of a heart 34, using a probe 24. A distal end 32 of the probe is assumed to have electrodes 22. The measured signals are used, among other usages, for creating a LAT map of at least part of wall tissue of heart 34 of a patient 26.

Typically, probe 24 comprises a catheter which is inserted into the body of patient 26 during a mapping procedure performed by a physician 28 using system 20. During the procedure patient 26 is assumed to be attached to a grounding electrode 23. In addition, electrodes 29 are assumed to be attached to the skin of patient 26, in the region of heart 34.

System 20 may be controlled by a system processor 40, comprising a processing unit 42 communicating with a memory 44. In some embodiments, a memory 44, which is included in system processor 40, stores a LAT and/or voltage map 62 of at least part of wall tissue of heart 34 of patient 26. Additionally or alternatively, memory 44 may store maps of other patients. Moreover, any other processor (i.e., not necessarily part of system 20) that comprises a memory may store one or more maps. Processor 40 is typically mounted in a console 46, which comprises operating controls 38, typically including a pointing device 39 such as a mouse or trackball, that professional 28 uses to interact with the processor.

Processor 40 (specifically processing unit 42) runs software, comprising a probe tracker module 30, an ECG module 36, and an arrhythmia simulation module comprising a LAT analysis module 35, to operate system 20 and/or for LAT analysis module 35 to run simulation (using LAT or adjusted LAT maps 62 stored in memory 44) of heart pacing so as to model arrhythmia. The simulated heart pacing might be achieved by the physician 20 or an assistant operator clicking on the screen in the desired location for simulated pacing or in any other manner. Proposed areas for simulated pacing might also be displayed by processor 40.

Results of the operations performed by processor 40 are presented to physician 28 on a display 48, which typically presents a graphic user interface to the physician, a visual representation of the ECG signals sensed by electrodes 22, and/or an image or map of heart 34 while it is being investigated. In an embodiment, LAT analysis module 35 present to the physician a LAT map updated with one or more locations on the map where a simulated arrhythmia originated from. The software may be downloaded to processor 40 in electronic form, over a network, for example, or it may, alternatively or additionally, be provided and/or stored on non-transitory tangible media, such as magnetic, optical, or electronic memory.

ECG module 36 is coupled to receive actual electrical signals from electrodes 22 and electrodes 29. The module is configured to analyze the actual signals and may present the results of the analysis in a standard ECG format, typically a graphical representation moving with time, on display 48.

Probe tracker module 30 typically tracks the location of distal end 32 of probe 24, within the heart of patient 26. The tracker module may use any method for location tracking probes known in the art. For example, module 30 may operate a magnetic-field based location tracking sub-system. (For simplicity components of such sub-system are not shown in FIG. 1.)

Alternatively or additionally, tracker module 30 may track probe 24 by measuring impedances between electrode 23, electrodes 29 and electrodes 22, as well as the impedances to other electrodes which may be located on the probe. (In this case electrodes 22 and/or electrodes 29 may provide both ECG and location tracking signals.) The Carto3® system produced by Biosense Webster (Irvine, Calif.) uses both magnetic field location tracking and impedance measurements for location tracking.

Using tracker module 30 processor 40 is able to measure locations of distal end 32. In addition, using both tracker module 30 and ECG module 36 the processor is able to measure locations of the distal end, as well as LATs of the actual electrical signals detected at these particular locations. For clarity, in the present disclosure and in the claims, measured locations of the distal end that do not have associated LAT measurements are herein termed non-LAT-locations, and are used only for generating the anatomical component of a three-dimensional (3D) LAT map of interior walls tissue of heart 34. Measured locations of the distal end having respective LAT measurements are termed LAT-locations, and are subsequently used for attempting simulating an arrhythmia.

Simulation of Heart Pacing for Modeling Arrhythmia

Figure 2:
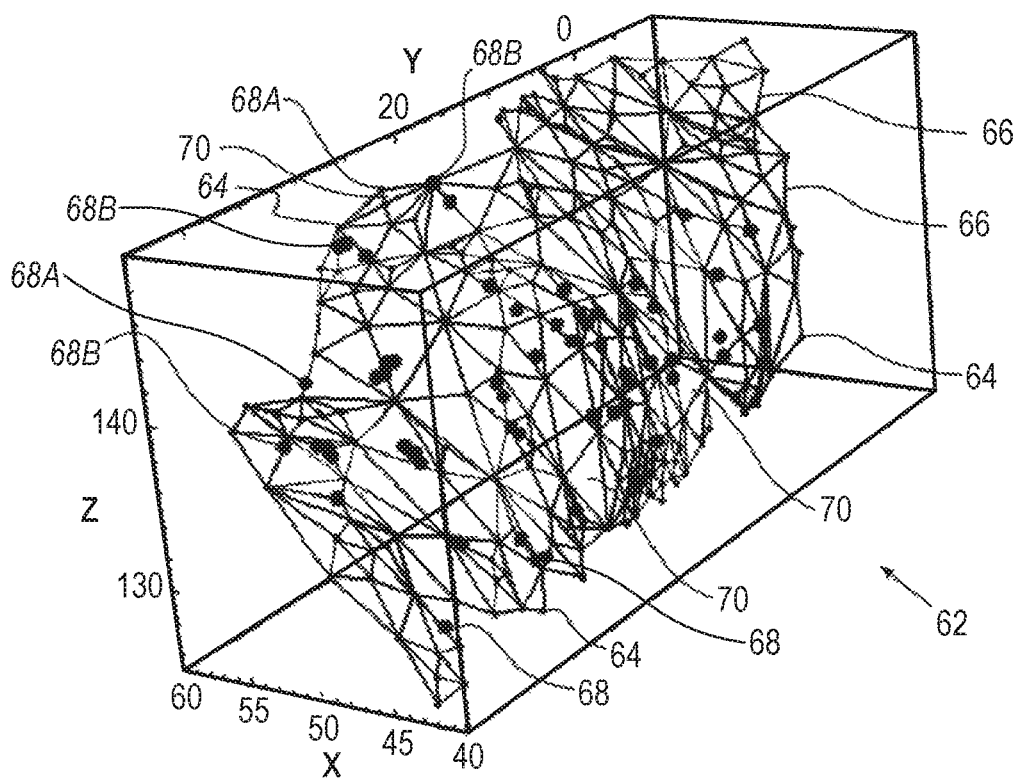
FIG. 2 is a schematic, pictorial illustration of a Local Activation Time (LAT) map of a heart, in accordance with an embodiment of the present invention.

FIG. 2 is a schematic, pictorial illustration of LAT map 62 of heart 34, in accordance with an embodiment of the present invention. For simplicity, only a portion of a complete map of interior walls tissue is shown in FIG. 2. LAT map 62 is formulated as a mesh comprising a multitude of non-LAT-location points 64, the positions of which have been evaluated by tracker module 30 so as to create the anatomical component of map 62. In an embodiment, processor 40 connects points 64 by straight inter-point lines 66 so as to form a mesh of connected planar triangles 70. Connected triangles 70 form a surface that approximates the heart interior wall tissue surface. Other methods of anatomical reconstruction may be applied, such as CARTO® SEG CT/MRI imports, and other modes of presentation of the reconstruction may be used, such a mesh produced from fast-anatomical-mapping.

Map 62 also shows LAT-locations 68, each LAT-location having an associated LAT value (referred to simply as "LAT"). Typically, LAT-locations and their associated LATs are evaluated at a different time period from the time used by processor 40 to generate the anatomical component of map 62. As for non-LAT-locations, LAT-locations are adjusted to the reference-time, among other reasons so as to correct for heart wall motion. In principle, LAT-locations 68 should be registered with surfaces of triangles 70, since both types of locations, LAT-locations and non-LAT-locations, should lie on the heart tissue wall.

The electrical activity of the heart may be thought of as a wave of electrical potential, which initiates at the beginning of every heartbeat at the sinus node, and which propagates through the cardiac muscle. At any point on a cavity wall of the heart, a LAT at that point is caused by the potential propagating past the point.

In LAT map 62, one or more LAT-locations 68 designate actual signal pacing locations, i.e., locations at which an actual electrical signal was injected by a catheter electrode 22 into the heart wall tissue in the process of creating the map. LAT-locations 68 designate measured locations where the resulting electrical activity (in response to the injected actual signal) were sensed, so as to measure the respective LAT values.

In an embodiment, LAT analysis module 35 applies simulated electrical activity propagation in order to identify by simulation of this electrical activity propagation, virtually paced locations 68A and 68B, which provide best temporal fit, between resulting (i.e., by the simulation) simulated LAT patterns at different locations 68, and a recorded clinical arrhythmia. For example, a best fit may be obtained between a virtual pacing resulting in virtual LAT map and virtual time interval and time intervals characteristic of the recorded arrhythmia.

In some embodiments, LAT analysis module 35 updates LAT map 62 during simulated stimulation with one or more locations estimated as potential sources of arrhythmia. LAT analysis module 35 further assigns grades to LAT locations that quantify a likelihood of these candidate locations being sources of the arrhythmia. LAT analysis module 35 numerically and/or graphically updates LAT map 62 with the grades attributed to the one or more locations. Simulated pacing locations 68A that receive highest grades may serve as priority locations for attempts by the physician, during a catheterization, to generate acquired signals that correspond to the recorded arrhythmia. Subsequently, the physician may ablate tissue in vicinity of clinically identified locations, so as to for example isolate such.

Figure 3:
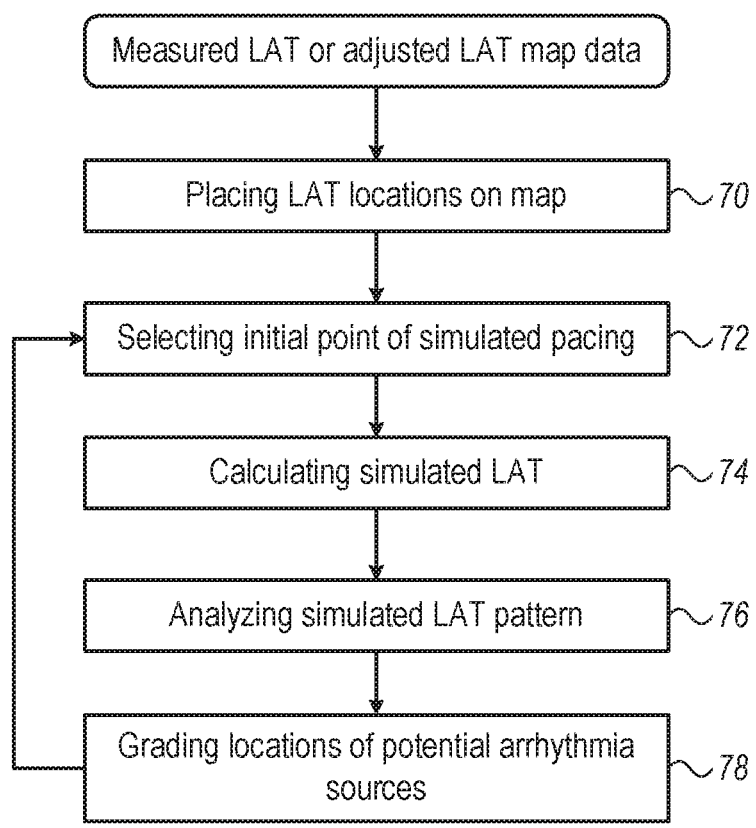
FIG. 3 is a flow chart that schematically illustrates a method for identifying on a LAT map, by simulation, locations that an arrhythmia may initiate from, in accordance with an embodiment of the present invention.

FIG. 3 is a flow chart that schematically illustrates a method for identifying on LAT map 62, locations that an arrhythmia may initiate from, in accordance with an embodiment of the invention. The locations are identified by creating simulated activation generated by virtual pacing, which yield results based on the pre-collected electro-anatomical signals.

The procedure may begin with, based on measured LAT map 62, building LAT map or adjusted LAT map, in which analysis module 35 calculates all LAT data and places it on map 62 stored in memory 44, at an initial step 70. Next, at a step 72, a virtual source 68A (i.e., an initial point of simulated pacing) is chosen by the processor or the user. LAT analysis module 35 considers the real propagation data and calculates the propagation from the virtual source at step 74.

The method now proceeds to an analyzing step 76, in which LAT analysis module 35 assign grades to a specific pacing position 68A that quantify a likelihood of the candidate location being source of the arrhythmia. In an embodiment, LAT analysis module 35 adds an indication, such as the grade or a graphical one, to LAT map 62, at an updating map step 78.

The procedure may be repeated by LAT analysis module 35 selecting another virtually paced location 68A, as the method returns to selecting initial point step 72.

The example flow chart shown in FIG. 3 is chosen purely for the sake of conceptual clarity. In alternative embodiments, various steps may be performed to assess locations of arrhythmia such as using alternative electrophysiological maps and/or simulation steps as well as performing the above in a different order.

Although the embodiments described herein mainly address the treatment of ischemic ventricular tachycardia, the methods and systems described herein can also be used in other applications, such as in any focal or reentrant arrhythmias.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A cardiac simulation method for identifying, estimating and grading locations on the cardiac surface from which an arrhythmia may originate, the method comprising:

storing, in a memory, a measured electrophysiological map of at least part of wall tissue of a heart of a patient, wherein the measured electrophysiological map comprises collected pre-acquired electro-anatomical data;

calculating, via a processor, simulated propagation of electrical activity from one or more candidate locations of potential arrhythmia on the measured electrophysiological map, using only real propagation data from the measured electrophysiological map;

based on the simulated electrical activity calculated in the simulation run by the processor, identifying and indicating to a user, one or more candidate locations on the wall tissue of the heart at which arrhythmia is suspected of originating, wherein identifying the one or more candidate locations further comprises comparing the simulated electrical activity with the actual electrical activity acquired in the heart of the patient that exhibits the arrhythmia, and finding the candidate locations that produce a best fit between the simulated electrical activity and the actual electrical activity; and updating the measured electrophysiological map with the identified candidate locations that produce the best fit.

2. The method according to claim 1, wherein storing the measured electrophysiological map comprises storing one or more of a Local Activation Time (LAT) map, a voltage map and an adjusted LAT map, and wherein the one or more locations comprise electro-anatomical locations on the measured electrophysiological map.

3. The method according to claim 1, wherein finding the best fit comprises finding a best temporal fit between the simulated electrical activity and the actual electrical activity.

4. The method according to claim 1, and comprising assigning the one or more candidate locations respective grades that quantify a likelihood of the candidate locations being sources of the arrhythmia.

5. The method according to claim 4, and comprising presenting the grades assigned to the one or more candidate locations to a user.

6. The method according to claim 5, wherein presenting the grades comprises updating the measured electrophysiological map with the grades assigned to the one or more candidate locations.

7. The method according to claim 1, wherein identifying the one or more candidate locations comprises receiving, via a user interface, user input indicative of the one or more candidate locations.

8. A cardiac pacing simulator for identifying, estimating and grading locations on the cardiac surface from which an arrhythmia may originate, comprising:

a memory configured to store a measured electrophysiological map of at least part of wall tissue of a heart of a patient, wherein the measured electrophysiological map comprises collected pre-acquired electro-anatomical data; and a processor, configured to:

calculate, via the processor, simulated propagation of electrical activity from one or more candidate locations of potential arrhythmia on the measured electrophysiological map, using only real propagation data from the measured electrophysiological map; and based on the simulated electrical activity calculated in the processor, identify and indicate to a user one or more candidate locations on the wall tissue of the heart, at which arrhythmia is suspected of originating by comparing the simulated electrical activity with the actual electrical activity acquired in the heart of the patient that exhibits the arrhythmia, and finding the candidate locations that produce a best fit between the simulated electrical activity and the actual electrical activity updating the measured electrophysiological map with the identified candidate locations that produce the best fit.

9. The simulator according to claim 8, wherein the stored measured electrophysiological map comprises one or more of a Local Activation Time (LAT) map, a voltage map and an adjusted LAT map, and wherein the one or more locations comprise electro-anatomical locations on the measured electrophysiological map.

10. The simulator according to claim 8, wherein the processor is configured to find the best fit by finding a best temporal fit between simulated electrical activity and the actual electrical activity.

11. The simulator according to claim 8, wherein the processor is configured to assign the one or more candidate locations respective grades that quantify a likelihood of the candidate locations being sources of the arrhythmia.

12. The simulator according to claim 11, wherein the processor is additionally configured to present the grades assigned to the one or more candidate locations to a user.

13. The simulator according to claim 12, wherein the processor is configured to present the grades by updating the measured electrophysiological map with the grades assigned to the one or more candidate locations.

14. The simulator according to claim 8, and comprising a user interface configured to receive user input indicative of the one or more candidate locations.

* * * * *